US011724009B2

(12) United States Patent
Paquin et al.

(10) Patent No.: US 11,724,009 B2
(45) Date of Patent: Aug. 15, 2023

(54) WIRE-FORMED BIO-ABSORBABLE IMPLANTS AND METHODS FOR ASSEMBLY

(71) Applicant: ZORION MEDICAL, INC., Zionsville, IN (US)

(72) Inventors: Mark Paquin, Indianapolis, IN (US); David Broecker, Zionsville, IN (US)

(73) Assignee: ZORION MEDICAL, INC., Zionsville, IN (US)

( * ) Notice: Subject to any disclaimer, the term of this patent is extended or adjusted under 35 U.S.C. 154(b) by 0 days.

(21) Appl. No.: 16/483,200

(22) PCT Filed: Feb. 5, 2018

(86) PCT No.: PCT/US2018/016904
§ 371 (c)(1),
(2) Date: Aug. 2, 2019

(87) PCT Pub. No.: WO2018/145029
PCT Pub. Date: Aug. 9, 2018

(65) Prior Publication Data
US 2019/0365957 A1  Dec. 5, 2019

Related U.S. Application Data

(60) Provisional application No. 62/454,202, filed on Feb. 3, 2017.

(51) Int. Cl.
A61F 2/89  (2013.01)
A61F 2/86  (2013.01)
(Continued)

(52) U.S. Cl.
CPC ........... *A61L 31/022* (2013.01); *A61L 31/148* (2013.01); *A61F 2/86* (2013.01); *A61F 2250/0098* (2013.01); *A61L 31/18* (2013.01)

(58) Field of Classification Search
CPC ........ A61F 2/86; A61F 2/89; A61F 2002/828; A61F 2210/0004; A61F 2250/0098;
(Continued)

(56) References Cited

U.S. PATENT DOCUMENTS 6,056,775 A * 5/2000 Borghi .................... A61F 2/954
606/195
6,083,257 A    7/2000 Taylor et al.
(Continued)

FOREIGN PATENT DOCUMENTS

CN    204600789 U    9/2015
EP    2582408 A2    4/2013
(Continued)

OTHER PUBLICATIONS

International Search Report and Written Opinion, International Application No. PCT/US2018/016904, dated Jul. 9, 2018, 16 pages.
(Continued)

Primary Examiner — Seema Mathew
(74) Attorney, Agent, or Firm — Quarles & Brady LLP

(57) ABSTRACT

Modularizable implants and stents made with bio-absorbable metal wire alloys ('bio-metals', e.g. magnesium and alloys), and methods for making such implants and stents. The stents or implants may include one or more wire-formed rings or comprise inter-connected cells that form nets that may serve as modules that are assembled mechanically into stents, without the need for certain manufacturing processes that may affect the durability and physical properties thereof. The wires may be formed into rings mechanically and held in place using joining cuffs, and/or adjacent wires may be secured to one other mechanically using joining cuffs to form nets which can be used as implants or formed into stents. The stents can include radiopaque portions, e.g. associated with one or more joining cuffs, to aid in the
(Continued)

positioning and evaluation of stents in the body by serving as visual indicators of alignment and expansion that can be detected using X-rays.

10 Claims, 14 Drawing Sheets

(51) Int. Cl.
    *A61L 31/02*     (2006.01)
    *A61L 31/14*     (2006.01)
    *A61L 31/18*     (2006.01)

(58) Field of Classification Search
    CPC ........ A61F 2/90; A61F 2/82; A61F 2002/821; A61F 2/915; A61F 2002/3008; A61L 27/58; A61L 31/148; A61L 31/18; C22F 1/06
See application file for complete search history.

(56) References Cited

U.S. PATENT DOCUMENTS

| | | | | |
|---|---|---|---|---|
| 6,113,628 | A * | 9/2000 | Borghi | A61F 2/954 606/198 |
| 8,574,286 | B2 * | 11/2013 | Wack | A61F 2/844 623/1.15 |
| 8,636,790 | B2 * | 1/2014 | Igaki | A61L 31/04 623/1.15 |
| 8,986,369 | B2 * | 3/2015 | Steckel | A61L 31/022 623/1.38 |
| 2005/0137692 | A1 * | 6/2005 | Haug | A61F 2/2439 623/2.11 |
| 2011/0184506 | A1 * | 7/2011 | Igaki | A61L 31/04 623/1.16 |
| 2011/0319977 | A1 * | 12/2011 | Pandelidis | C22F 1/06 623/1.42 |
| 2014/0200656 | A1 * | 7/2014 | Thomas | A61F 2/06 623/1.34 |
| 2016/0310303 | A1 * | 10/2016 | Thapliyal | A61F 2/966 |

FOREIGN PATENT DOCUMENTS

| | | |
|---|---|---|
| EP | 3120877 A1 | 1/2017 |
| JP | 11507567 A | 7/1999 |
| JP | 2013529507 A | 7/2013 |
| WO | WO-9641591 A1 * 12/1996 | ............... A61F 2/86 |
| WO | 0115632 A1 | 3/2001 |
| WO | 2011163236 A2 | 12/2011 |
| WO | 2016136375 A1 | 9/2016 |
| WO | 2016172629 A1 | 10/2016 |

OTHER PUBLICATIONS

First Office Action from corresponding Chinese Patent Application No. 201880010289.1 dated May 21, 2021 (11 pages) (English translation included).
First Office Action from corresponding Japanese Patent Application No. 2019-542126 dated Oct. 26, 2021 (12 pages) (English translation included).
Examination Report from corresponding European Patent Application No. 18706073.6 dated Sep. 29, 2021 (6 pages).
Korean Intellectual Property Office, Office Action, Application No. 10-2019-7024688, dated Dec. 16, 2022.

* cited by examiner

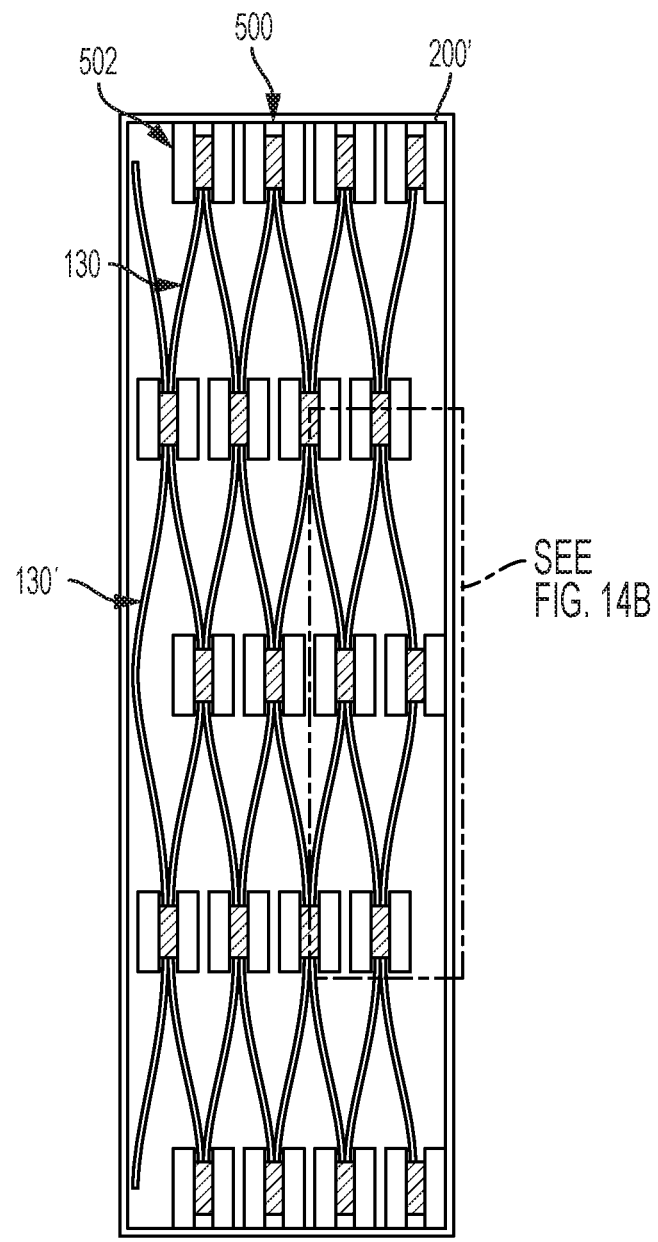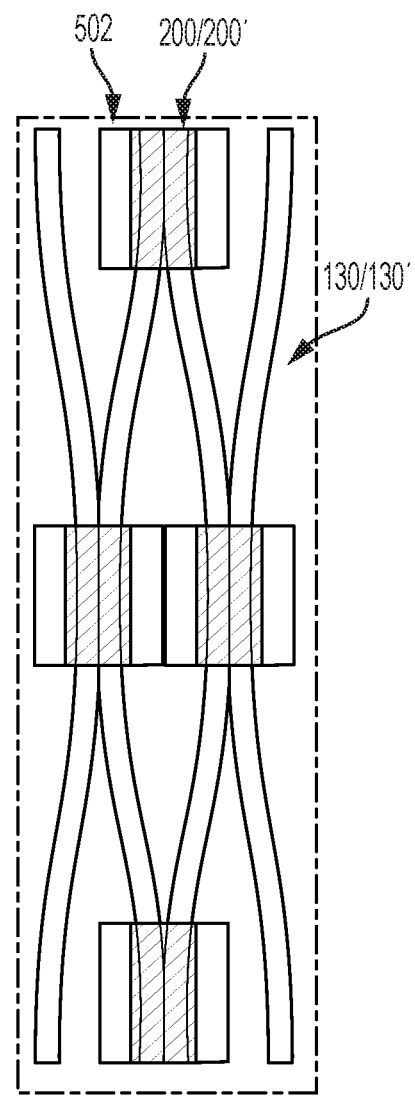
FIG. 14A
FIG. 14B

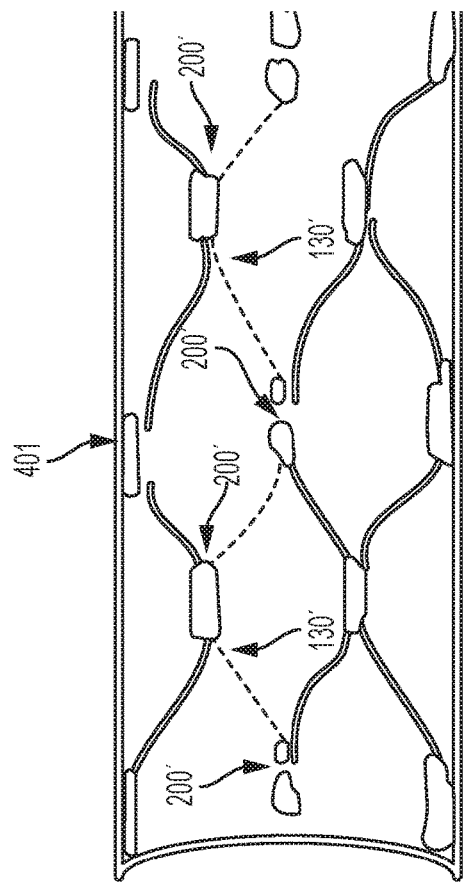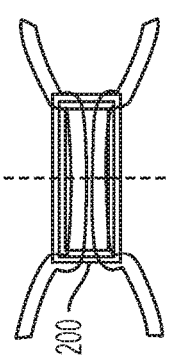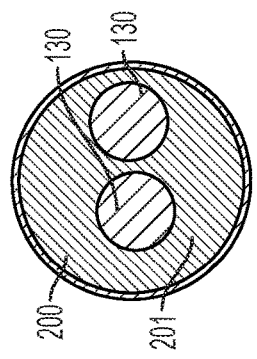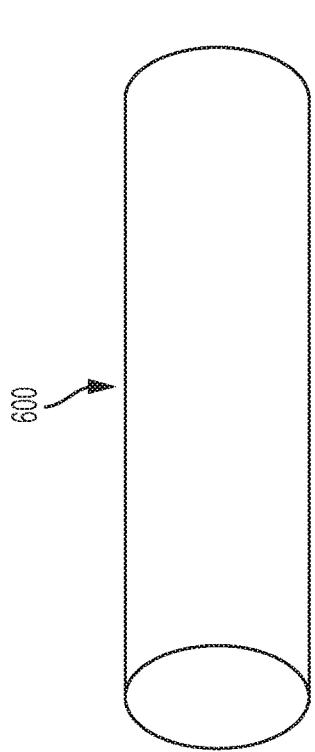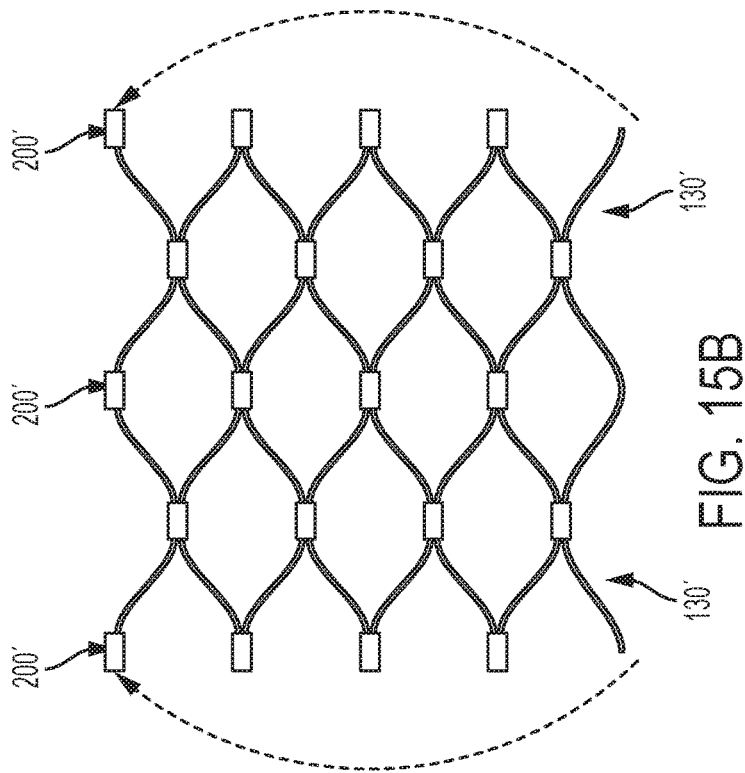

WIRE-FORMED BIO-ABSORBABLE IMPLANTS AND METHODS FOR ASSEMBLY

CROSS-REFERENCE TO RELATED APPLICATIONS

This application is based on, and claims the benefit of, U.S. Provisional Patent Application No. 62/454,202, filed Feb. 3, 2017, which is hereby incorporated herein by reference in its entirety for all purposes.

FIELD OF THE INVENTION

This document concerns an invention relating generally to bioresorbable medical devices, and more specifically, to bioresorbable implants such as stents that may include one or more wire-formed structures, may be modularized, and/or may be assembled without the need for manufacturing processes that could have undesirable effects on bioresorbable metals, for example processes that alter the mechanical and/or resorption properties of bioresorbable materials.

BACKGROUND OF THE INVENTION

Traditional stents, which can be inserted into a cavity or duct (such as a blood vessel) and expanded to prevent or alleviate blockages, normally remain in the body indefinitely unless removed via a subsequent surgical procedure. In contrast, stents that are biodegradable (also referred to as bioabsorbable or bioresorbable, used interchangeably) can disintegrate in the body, and thus are normally not surgically removed at the end of their functional life. To promote bio-absorbability, such stents may include materials that may dissolve or degrade in the body over time, with nominal or no long-term negative effects on the patient. Examples of such materials include bioresorbable metals ('bio-metals'), such as magnesium, zinc, and iron, and alloys thereof. Use of bioresorbable metals can provide certain desirable characteristics of metallic compounds, such as structural support, while disintegrating safely so as to not require surgical intervention to remove, e.g. in the event of device failure. Because surgical interventions are not without risk of complications for patients, reducing the need for unnecessary surgeries (e.g. to remove an implanted stent) is preferable. Furthermore, in certain cases a patient may be subjected to additional interventions as a result of the presence of a permanent implant, e.g. to correct restenosis. Reducing interventions and surgeries can achieve significant savings in cost and time and enhance outcomes.

However, although they can provide substantial benefits, devices such as stents that are made with bio-metals are engineered to have certain bio-mechanical and bio-resorption properties that should be preserved and maintained throughout the assembly and implantation process. Thus, there is a need to improved methods and apparatus for forming bio-metal implants such as stents."

SUMMARY OF INVENTION

Exemplary versions of the present invention relate to implants such as stents made with wires having bio-absorbable metals ('bio-metals') such as magnesium and its alloys. The ends of the wires may be secured to each other mechanically (using, for example, a securing mechanism such as a joining cuff) in such a way so as not to affect the durability and physical properties of the end product. In various configurations, the stents or other implants may include one or more wires or wire-formed rings. Exemplary versions of the bio-metallic implants (e.g. stents) may include modules (such as the wire-formed rings) that can also be assembled mechanically (using, for example, a securing mechanism such as a bridging cuff). In other exemplary versions, the stents or other implants can include radiopaque ('RO') portions (such as the joining and bridging cuffs) configured to aid in the positioning and evaluation of exemplary stents or implants in situ by serving as visual indicators of alignment and expansion. In yet other exemplary versions, the wire-formed structure can be assembled or woven to form a net, using the aforementioned joining cuffs at multiple points of contact between the wires.

In one embodiment, the invention provides a bio-metal implant including a first magnesium alloy wire. The first magnesium alloy wire is adjacent a second magnesium alloy wire at a first connection point, the first magnesium alloy wire coupled to the second magnesium alloy wire at the first connection point using a first joining cuff of a plurality of joining cuffs, and the first magnesium alloy wire and the second magnesium alloy wire being shaped to form at least a portion of the bio-metal implant.

In another embodiment, the invention provides a bio-metal implant including a plurality of magnesium alloy wires formed into a tube. Each of the plurality of magnesium alloy wires is secured to two adjacent magnesium alloy wires of the plurality of magnesium alloy wires by two respective subsets of joining cuffs of a plurality of joining cuffs.

In yet another embodiment, the invention provides a bio-metal implant including a first sinusoidal wire having ends secured together to form a first ring. The first sinusoidal wire includes a bio-metal and the ends of the first sinusoidal wire are secured together without use of heat.

In still another embodiment, the invention provides a method of assembling a bio-metal stent. The method includes joining a plurality of magnesium alloy wires into a net by securing each of the plurality of magnesium alloy wires to an adjacent magnesium alloy wire of the plurality of magnesium alloy wires using a subset of a plurality of joining cuffs. The method also includes forming the net into a tube shape by wrapping the net around a mandrel. The method further includes securing opposing edges of the net using a magnesium alloy end wire by attaching the magnesium alloy end wire to the opposing edges of the net.

In yet another embodiment, the invention provides a method of assembling a bio-metal stent. The method includes providing a first sinusoidal wire having two ends and including a bio-metal; shaping the first sinusoidal wire into a first ring; and securing the two ends of the first sinusoidal wire together without use of heat.

In still another embodiment, the invention provides a method of implanting a stent in a subject. The method includes providing a stent including a tubular structure including a plurality of wires connected by a plurality of joining cuffs, each of a subset of joining cuffs of the plurality of joining cuffs having a radiopaque marker. The method also includes placing the stent within a luminal space of the subject. The method further includes obtaining a first image of the luminal space showing first locations of the subset of joining cuffs having the radiopaque markers. The method also includes expanding the stent within the luminal space. The method further includes obtaining a second image of the luminal space showing second locations of the subset of joining cuffs having the radiopaque markers, the second locations of at least two of the subset of joining cuffs having the radiopaque markers being further apart than the second locations of the at least two of the subset of joining cuffs having the radiopaque markers.

Further advantages and features of the invention will be apparent from the remainder of this document in conjunction with the associated drawings.

DESCRIPTION OF THE DRAWINGS

FIG. 14A shows use of a fixture for assembly of adjacent-parallel (flattened) wires into a net structure for use as an implant or for forming a net-based stent.

FIG. 14B shows an inset from FIG. 14A showing how several wires are threaded through joining cuffs to form a portion of the net structure.

FIGS. 15A-15C represents steps of an exemplary wire-forming process of using a wire-forming fixture to produce a net for use as an implant or for forming a net-based stent such as that shown in FIG. 12.

FIG. 15D shows a single cuff with sealing material therein.

FIG. 15E shows a cross-sectional view of the cuff of FIG. 15D.

DETAILED DESCRIPTION OF THE INVENTION

Figure 1:
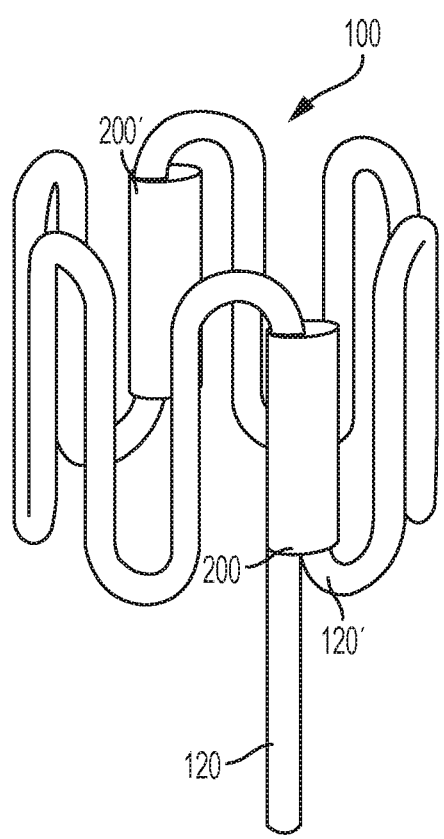
FIG. 1 is an exemplary sinusoidal wire-formed ring, with ends secured using an exemplary circumferential joining cuff.

In some embodiments, a wire having a sinusoidal shape may be formed into a ring; one or more such rings may be used (e.g. by joining the rings on their edges) to form a ring-based stent 300. In other embodiments, a plurality of wires may be joined by a plurality of cuffs to form a net 401, which may be used as an implant in the net form or the net may be rolled into a tube shape and secured to form a net-based stent 400.

In accordance with this illustrative embodiment, the wires to produce either embodiment of the net 401 or stent 300, 400 may be formed from a bio-absorbable metal component or alloy (i.e. a 'bio-metal'). While the bio-absorbable metal components used to form the wire in accordance with the present teachings can be fabricated from a variety of absorbable metallic materials, in accordance with certain aspects, the metal components include pure and alloyed metals in order to achieve partial or full breakdown and absorption over a period of time (e.g. which can be about 1 month for plain, uncoated wire implant materials up to several months, or as much as a year for coated implants, depending on factors such as the coating and site of implant) sufficient for tissue healing. Illustrative metal components that may be used in accordance with the present teachings include, but are not limited to, pure metals and alloys of magnesium, zinc, and iron, and particularly alloys that are substantially free of rare earth metals. While incorporation of rare earth elements facilitates fabrication of bio-metal devices, utilization of alloys substantially free of rare earth metals minimizes the potential adverse and toxicological effects of these materials when implanted in the body. As used herein, in certain embodiments the term 'substantially free of rare earth metals' is intended to mean that less than 500 ppm of the metallic alloy includes rare earth metals. To this end, it should be understood that the metallic alloy components of the present teachings preferably have a high purity and fine grain size in order to achieve consistent strength and in vivo degradation rates in thin-walled structures regardless of the alloy that is used. As those of skill in the art will understand and appreciate herein, keeping the metallic alloy components substantially free of rare earth metals may allow the implant such as a net or stent to be naturally absorbed by the body while having an additional benefit that the structural integrity of the implant will not be negatively impacted by the inherently corrosive properties of the rare earth metals.

For magnesium-based absorbable metals used in various embodiments of the presently-disclosed apparatus and methods, either pure magnesium or high-purity alloys that contain one or more of lithium, calcium, manganese, zinc, iron, aluminum, or combinations thereof may be used. In accordance with certain aspects of the present teachings, an alloy wire may include more than 50% by weight of one or more metals selected from: magnesium, iron, zinc, calcium, and manganese. In accordance with other embodiments in which alloys of magnesium are used to form an alloy wire, the magnesium alloy may contain between about 1% and about 25% by weight lithium. Whatever specific components are used to form alloy wires, the resulting alloy wires should be formable into the various shapes as disclosed herein, for example stents or other implants that include wires formed into sinusoidal shapes, rings, and/or net structures. In various embodiments, the wire may have a thickness between about 10 microns and 300 microns, and in particular embodiments the wire may have a thickness between about 50 microns and about 150 microns. In certain embodiments in which a stent is made for use in coronary arteries, the wire that is used may have a thickness of about 150 microns, and in other embodiments in which a stent is made for use in peripheral blood vessels, the wire that is used may have a thickness of about 150-200 microns.

Various wire forming methods are generally known within the art, and as such, the fabrication methods envisioned by the present teachings are not intended to be limited herein. According to certain aspects herein, the wire can be processed by conventional wire forming methods that utilize a rotating pin table or a table of fixed pins to impart a particular shape (e.g. sinusoidal) on the wire. In addition, if desired, the final shaped wire, net, and/or stent structure may be electro-polished to remove surface contaminants, as well as to reduce its final diameter. Moreover, while not required herein, in accordance with certain aspects of the present teachings, it may also be beneficial to smelt the metallic alloys under vacuum and in pyrolitic carbon molds in order to minimize impurities. Finally, as discussed further below, a wire-forming fixture may be used to facilitate formation of a net. Additional wire compositions and wire-forming methods are disclosed in US Patent Appl. Publ. No. 2015/0272753, which is incorporated herein by reference in its entirety for all purposes.

In various embodiments the methods and apparatus disclosed herein are directed to producing bioabsorbable wire-based implants such as stent structures using magnesium-based alloys (such as those discussed above) to take advantage of the bioabsorbability of these highly engineered alloy materials. However, it is important that the magnesium alloy not be exposed to manufacturing methodologies that will adversely affect the biomaterial properties of the bio-absorbable alloy as this can alter the properties of the alloy, for example rendering it brittle or imparting unwanted points of device failure. In general, excessive heat may change factors such as mechanical properties of the metal including grain size, microstructure, ductility, and/or strength, and the particular temperature and effects may depend on the metal or alloy, the thickness of material (e.g. wire), and/or the application.

Although bio-metals can provide substantial benefits, stents made with bio-metals pose manufacturing challenges due in large part to their chemical compositions. While stents made from conventional, non-degradable metals can be subjected to well-characterized, standard, and wear-free processes, such as laser cutting and welding, these same processes can adversely affect bio-metals. For example, laser cutting of magnesium tubing that is extruded, highly pure, and free of rare earth elements can result in heat zones that may affect the material composition of the alloy, impacting the end-product's durability and physical properties. Similar undesirable outcomes can be experienced as a result of welding, which can heat the metals to temperatures of up to about 2000° C. For example, magnesium is a brittle element, and the physical defects arising from spot welding can be amplified for magnesium alloys, leading to internal and surface cracking, and ultimately can affect the durability and physical properties of the desired product. Similarly, temperatures required for annealing of metals, which are in a range of 250° C.-750° C., can also cause degradation of bio-metals. Consequently, high-heat manufacturing processes tend to compromise the integrity of bio-metallic medical devices, in part by affecting the grain size such that the requirement for small grain size is no longer met, at least for certain portions of the device.

On the other hand, the presently-disclosed methods and apparatus employ procedures that function either at ambient temperatures or at moderately warm temperatures that are much lower than the temperatures cited above and as a result do not adversely impact bio-metals. For example, some polymers may need slightly elevated temperatures to promote curing of the polymers, however these temperatures are generally less than 100° C. Similarly, in embodiments in which joining cuffs are fitted onto wires using heat-shrinking, the temperature range for heat-shrinking for certain materials (e.g. PLA, PLGA, or PCL) are less than 150° C., which is sufficiently low that it will not have an adverse impact on the bio-metals.

For conventional non-absorbable metal wire form based stents, this is typically achieved by spot welding adjacent rings through a laser or resistive welding process. These processes, however, are highly problematic for absorbable metal wire forms (such as magnesium based alloy systems); particularly as the magnesium surfaces rapidly form oxide layers that in turn inhibit strong metal to metal bonds from being formed. Welding of fine magnesium structures is further complicated by the material's intrinsic high thermal conductivity, such that heat energy applied to the local weld area is rapidly dissipated to the entire structure. In addition, even if a mechanical bond could be formed, the welding zone significantly changes the microstructure of the magnesium based alloy, thereby resulting in local embrittlement, undesirable axial stiffness, and non-uniform biodegradation rates.

In various embodiments a polymer surface coating, selected from a synthetic or natural absorbable polymeric component, may be applied to the wire and/or to the net 401 or stent 300, 400 at any of the stages of assembly. The polymer surface coating may impart advantages on the coated material such as prolonging the absorption time (e.g. compared to wire alone) and/or reducing potential galvanic reactions, e.g. between the wire and bodily fluids. The polymer surface coating may include synthetic and natural polymers selected from, but not limited to, aliphatic and cyclic polyesters, polyanhydrides, polycarbonates, and polypeptides such as collagen, elastin or gelatin. In some embodiments, absorbable polymers that can be used in accordance with the present teachings include synthetic linear polyesters, which have mechanical properties and established clinical uses and biocompatibility, as well as an ability to be processed by melt (extrusion) or solvent (spray coating) methods. These polymers may be synthesized from a variety of monomers such as lactic acid (PLA), glycolic acid (PGA), caprolactone (PCL), diaxanone (PDO), and other close derivatives. These monomers may also be combined during polymerization to form co-polymers (e.g. PLGA is a copolymer of PLA and PGA), with relative fractions controlled to influence properties such as crystallinity, degradation rate, and thermal stability. In certain embodiments, polymers based on two or more monomer types may be physically blended to achieve improved elasticity or altered absorption rate. In accordance with certain aspects of the present disclosure, the polymer surface coating may include a linear polyester high polymer selected from one or more of polylactic acid, polyglycolic acid, polydioxanone, polytrimethylenecarbonate and copolymers and blends thereof. In various embodiments, these polymer coatings may include (e.g. may be co-formulated with), or be further coated by, therapeutic agents, such as those discussed below.

In certain embodiments, various therapeutic agents that may be used (e.g. applied to the implant or stent as a coating by coating, spraying, or other methods known to those skilled in the art) with the presently disclosed bio-metal implants including, but not limited to, anti-restenotic agents, anti-stenotic agents, antiproliferative agents, immunomodulators, antithrombotics, antioxidants, estrogen, growth factor inhibitors, antisense oligonucleotides, collagen inhibitors, chemotherapeutic agents, and combinations thereof. In addition, the therapeutic agents can be one or more drugs selected from one or more of paclitaxel and related taxanes, rapamycin, sirolimus, everolimus, tacrolimus, heparin, and benzalkonium heparinate.

Ring-Based Bio-Metal Stents

Figure 2:
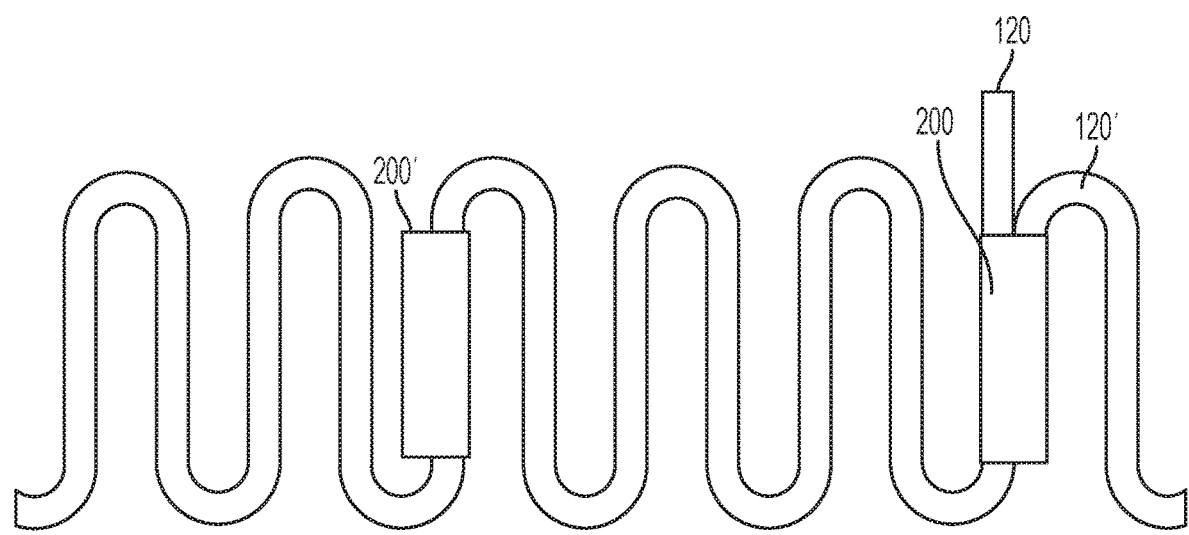
FIG. 2 depicts a flat-view representation of the wire-formed ring configuration of FIG. 1, with the sinusoidal wire shown flattened into a two-dimensional plane.

Referring to FIGS. 1 and 2, in some embodiments an exemplary wire-formed ring 100 used to make ring-based stents 300 extends from wire/ring tail 120 to end-tail 120'. The ring 100 in FIG. 1 may be formed by bending a wire (e.g. a wire having a sinusoidal shape) into a closed loop and securing the loop in place using a joining cuff 200, where one or both of a wire tail 120 at one end of the wire and an end-tail 120' at the other end of the wire are placed into the cuff 200. A single ring may be used, or two or more such rings may be joined together, to form a ring-based stent 300.

The wire used to form rings 100 may be provided with, for example, a generally 'sinusoidal' shape, or it may be curved or wound in another oscillatory or repetitive fashion. It is noted that the use of the term sinusoidal is not intended to suggest that the shape of the wire must necessarily fit a sine function or any other geometric function or equation, although the wire may be provided with a regularity or other suitable pattern that may, for example, be interfittable with, or otherwise complementary to, adjacent rings in order to enable modularization of rings in a stent. For convenience, the term 'sinusoidal' in this disclosure is used to generally encompass all such various shapes and configurations. In general, the wire includes a plurality of bends or curves which permit a stent made from the wire to be expanded into position, for example within a patient's blood vessel.

In one embodiment, the wire tail 120 may be mechanically secured to end-tail 120' via a joining cuff 200 to provide a 'ring' configuration for the sinusoidal wire. The joining cuff 200, which may be tubular or generally cylindrical with openings at opposing ends, may receive the wire tail 120 and end-tail 120' therein through the same (e.g. as depicted in FIGS. 1 and 2), or through different (opposing), ends. It is noted that the joining cuff 200 need not have a tubular 'cuff-like' configuration, but rather could be replaced with any sort of mechanically-adjoining structure or connecting means that includes, without limitation, one or more of a clip, fitting, joint, coupler, splicer, link, adhesive, and/or other connector allowing for the two ends of the wires to be movably or immovably secured to each other. Advantageously, the use of a mechanical/adjoining mechanism/means maintains and preserves the durability, integrity, and/or reliability of devices made with bioresorbable metals in a way that does not require use of elevated heat or other manufacturing procedures that could degrade the bio-metals.

As will be further discussed below, the ring 100 could be sized or configured to singularly serve as a stent on its own, or it could be one unit/module in a (modularized) stent that includes two or more rings/units/modules. It is noted that the wire tail 120 may extend out from the joining cuff 200 (whereas the end-tail 120' need not extend out from the joining cuff 200, or otherwise may be shorter), allowing the longer wire tail 120 to be more easily received in another cuff of an adjacent ring in a stent (as further discussed below). Because ring 100 as depicted in FIGS. 1 and 2 includes one wire tail 120 (which protrudes from the joining cuff 200) and one shorter end-tail 120' (which does not protrude from the joining cuff 200), rather than two wire tails 120, the ring 100 in FIG. 1 is well-suited to be an 'end piece' that is situated at a terminus of a stent. Ring 100 of FIG. 2 may be assembled into a stent alongside an adjacent ring, the stent extending generally in the direction of the ring tail 120 when secured to a second ring 100. That is, in this version, the wire-formed ring variation is an 'end-ring' configuration with the end-tail 120' tucked into joining cuff 200. It is also noted that the ring 100 in FIGS. 1 and 2 also includes an elongated bridging cuff 200', which will be further discussed below, and which could optionally be excluded in a stent formed of a singular ring 100 (i.e., a stent with only one unit/module and no adjacent units/modules) that includes two end-tails 120'. It is noted that, in certain configurations, joining cuffs 200 and bridging cuffs 200' may be similar (or substantially identical) structurally, but they differ functionally based on whether they secure ends of a ring (joining cuffs 200) or secure two rings together (bridging cuffs 200'). In general the cuffs 200 join together two portions of wire (from the same or different wires) at a connection point between the wires, i.e. a point where the wires are in proximity and possibly in contact and where the cuff helps to stabilize and maintain the wire(s) in this position.

Figure 3:
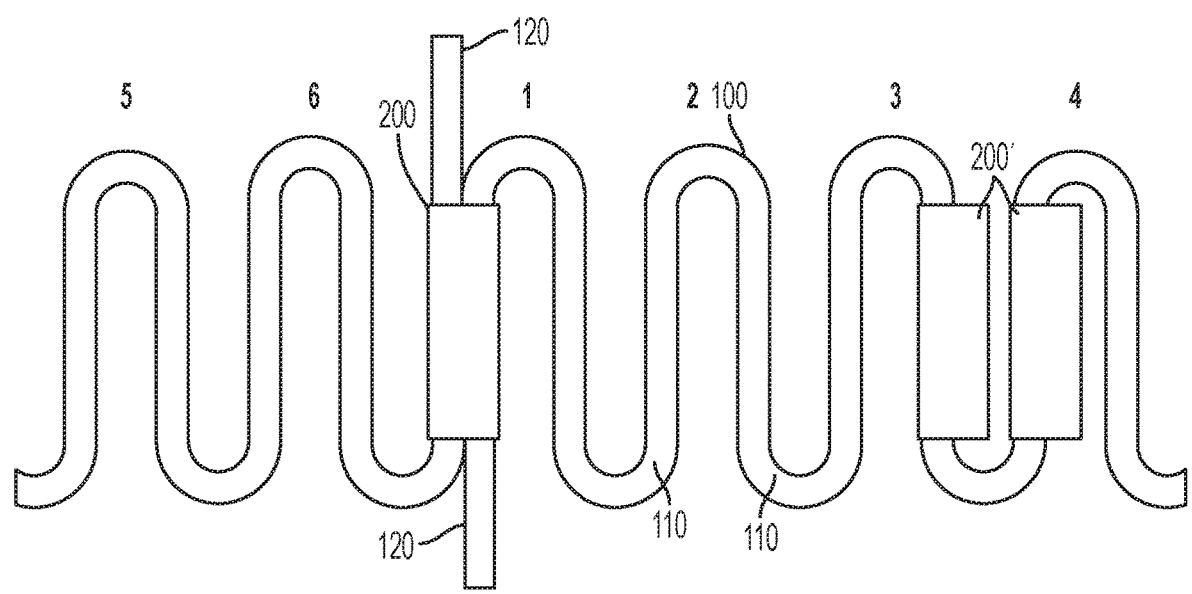
FIG. 3 provides a 'flat-view' representation of an alternative, six-crown wire-formed configuration with two wire tails secured to each other using a joining cuff.

FIG. 3 provides another wire-formed ring variation with two ring tails 120 secured by a joining cuff 200. Because there is no end-tail 120', this wire-formed ring is well-suited for being disposed between two other rings in a modularized stent. Thus, if the stent were to have three units, for example, the two rings between which the ring is disposed may be 'end rings' with one ring tail 120 and one end-tail 120'. In the version depicted in FIG. 3, the 'wavy' wire includes six 'crowns' (the crowns being defined by the curved sections of the wire), each crown having an upper crown portion 102 and a lower crown portion 106 at opposing ends of a strut 110. The numbers 1 through 6, above the apices of each crown (adjacent to the upper crown portions 102), represent the number of crowns in the ring. It is noted that any suitable number of crowns could be used to achieve various configurations for different applications, and that adjacent modules of a stent preferably have interfittable rings having the same number of crowns, but all the rings of a stent need not necessarily be identical. As shown in the version of FIG. 3, two aligned (i.e., substantially parallel) bridging cuffs 200' are positioned at two adjacent struts 110.

In certain embodiments the basic repeating unit of the sinusoidal wire may be described, for example as depicted in various figures, as having a substantially 'J' shape formed by one of the crown portions (102 or 106) in combination with a strut 110, with twelve such units (pieces) extending end-to-end to form the six crowns of FIG. 3, for example. The configuration of the wire, however, need not have such a repeating pattern, and each basic unit can be different from adjacent units to provide crowns that are not identical in shape but rather that may vary in width, height, pitch, angle, etc. Also, the struts 110, although shown as being substantially linear, could instead have a curved, wavy, sinusoidal, angled, or other shape in alternative versions.

Figure 4:
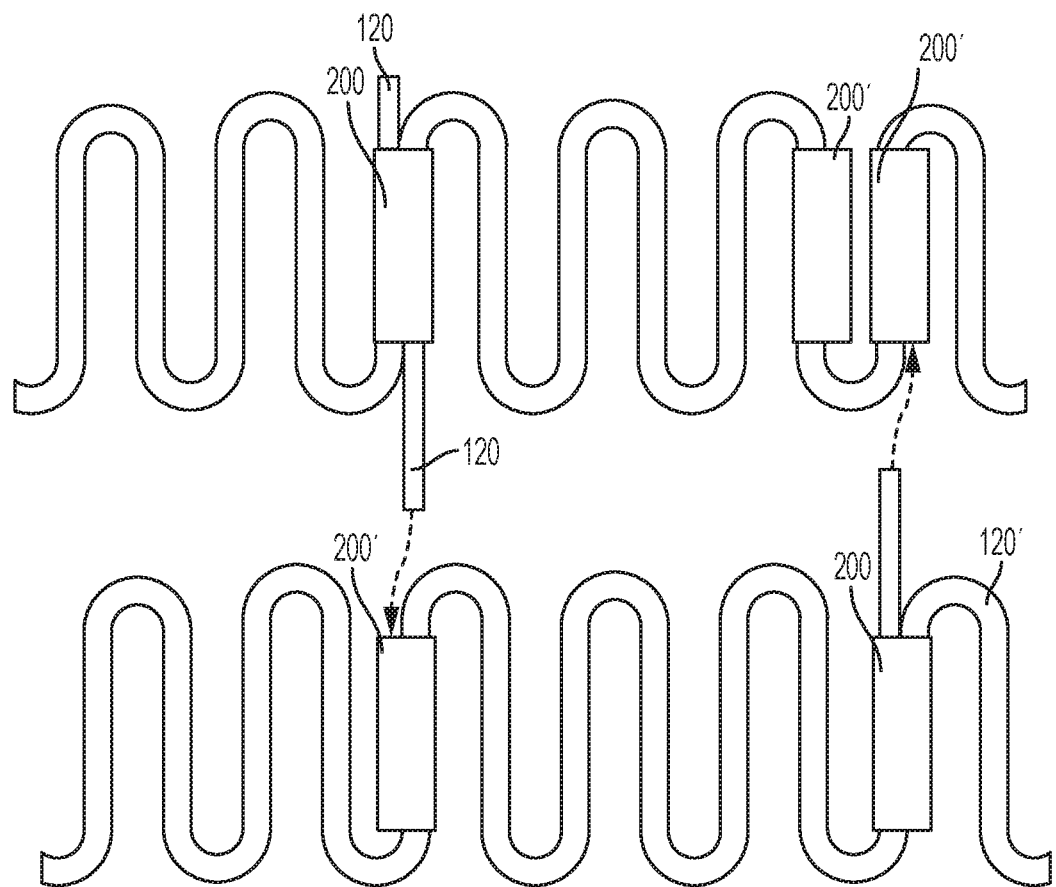
FIG. 4 depicts assembly of two adjacent (flattened) rings by insertion of a wire tail of one ring into a joining cuff of an adjacent ring.
Figure 5:
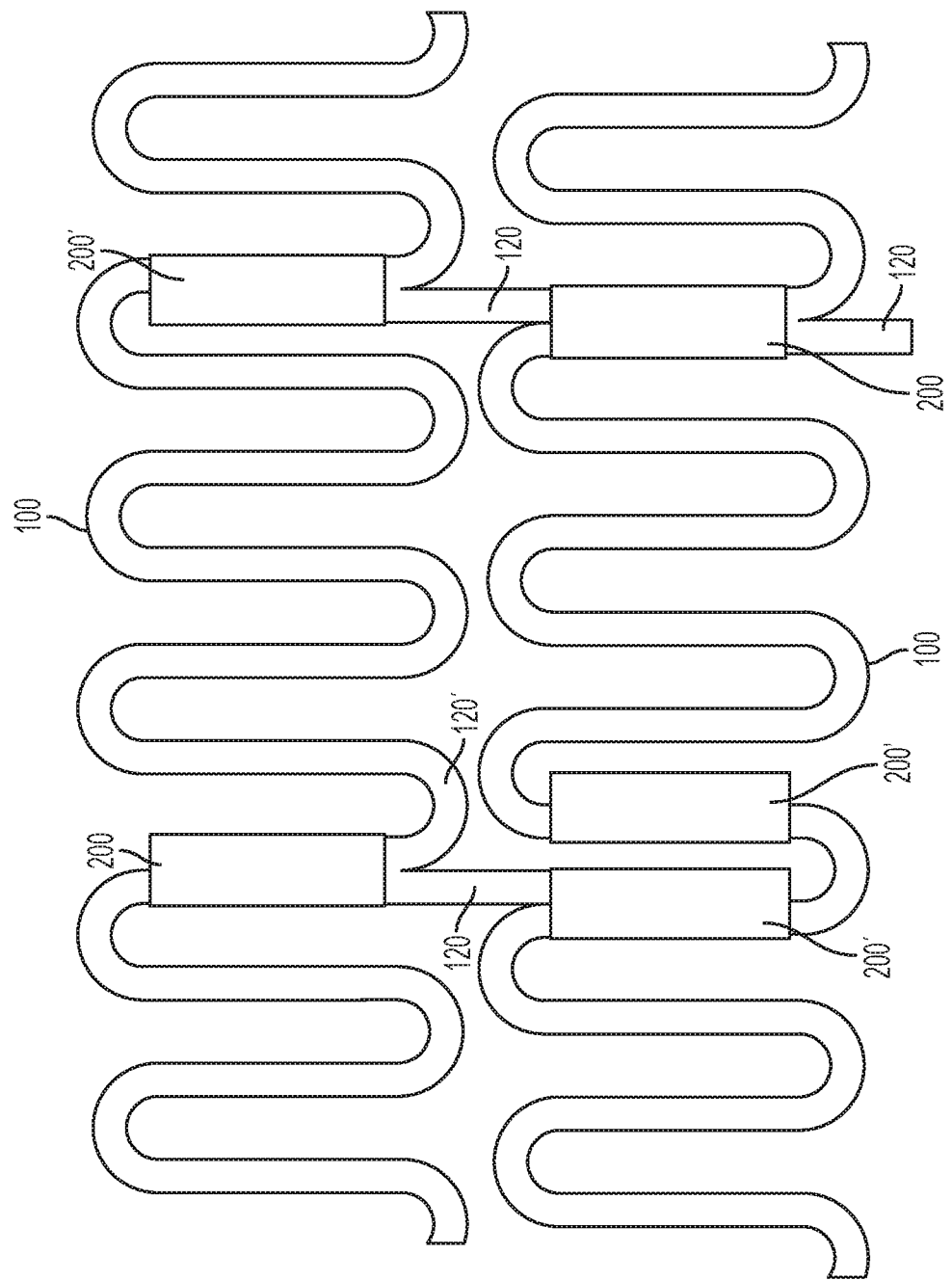
FIG. 5 shows the two flattened rings of FIG. 4 secured to each other mechanically to provide two adjoined rings.

FIG. 4 depicts assembly of two adjacent rings by inserting (e.g. tucking or sliding) wire tails 120 into bridging cuffs 200' pre-loaded on an adjacent ring, to achieve the two adjoined adjacent rings depicted in FIG. 5. Although FIGS.

Figure 6:
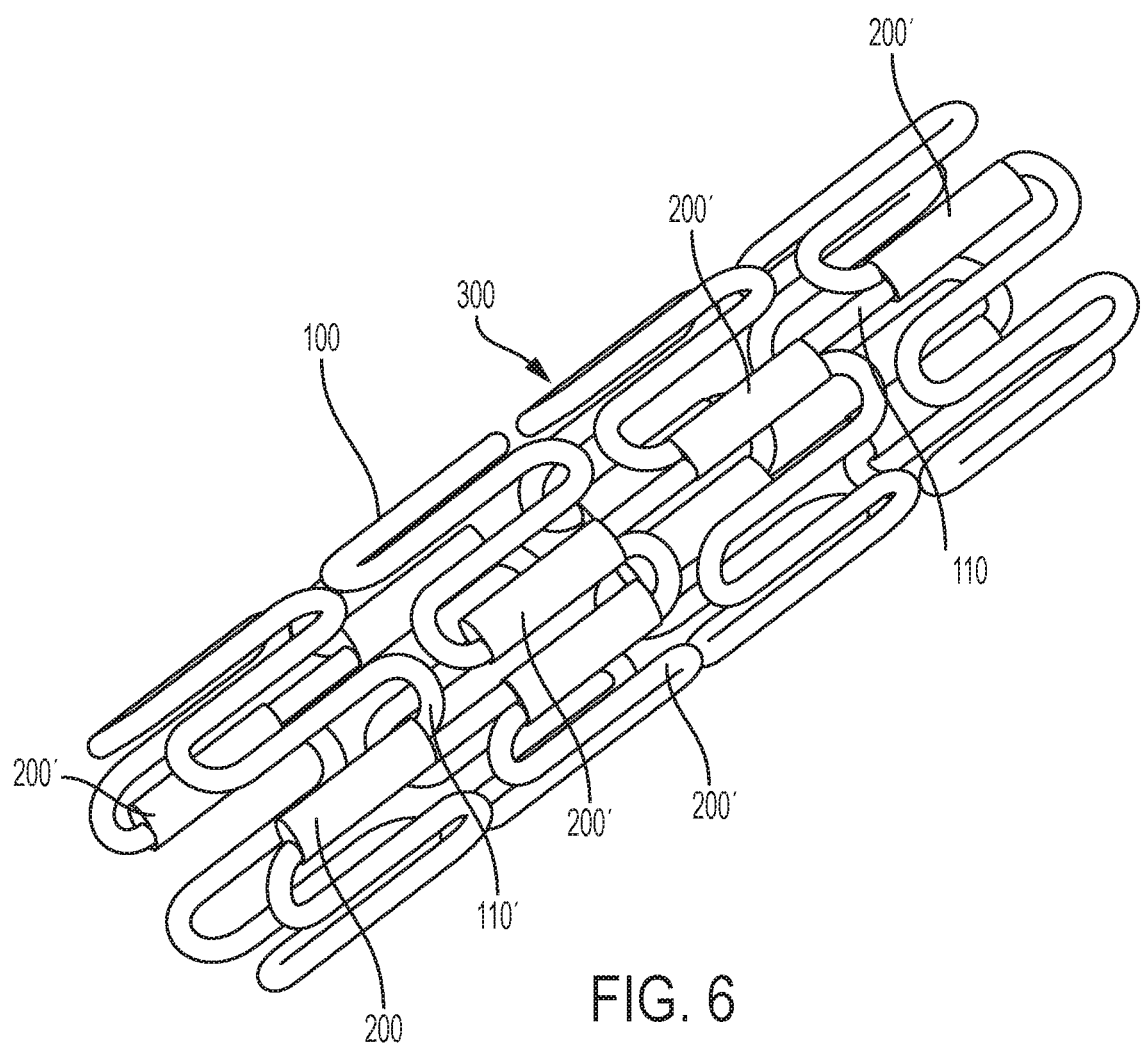
FIG. 6 is a perspective view of a four-ring, cylindrical stent, with spines defined by joining and/or bridging cuffs aligned such that long axes of the spines are aligned in parallel in the stent. The cuffs may include radiopaque materials such that they appear as the 'backbone' of the elongated stent and can thus provide a visual indication of the orientation of the stent using various imaging techniques (such as fluoroscopic imaging).

4 and 5 are depicted in flattened views, the attachment of wire tails into bridging cuffs 200' may be performed after the respective wires have been formed into three-dimensional rings, such as that shown in FIG. 6.

FIG. 6 is a perspective view of a four-ring, sinusoidal wire-formed, modularized cylindrical stent 300 formed according to the disclosed procedures. The joining cuffs 200 and bridging cuffs 200' in the final assembled stent 300 may be aligned such that they form a longitudinal 'spine' along a portion (or substantially all) of the length of the stent 300, on one or more sides thereof. The stent 300 may include one or more additional longitudinal spines along a portion of the length of the stent 300 at various other positions. For example, a second spine may be located on an opposing side (i.e., approximately 180 degrees around the cylindrical stent structure with respect to the first spine). That is, parallel spines of cuffs (200 and 200') may run along both sides of the wire-formed ring-stent at an approximately 180 degree (or other amount) separation.

As suggested above, placement of the cuffs 200, 200' may create a substantially (or effectively) linear array, or spine, along both sides of the wire-formed ring stent 300. Similar arrays or spines of cuffs may also be present with the diamond-shaped cells of the wire-formed net stent 400, discussed further below. Using either type of stent (ring-based or net-based), a radiopaque material such as platinum-iridium may be included in a subset of the cuffs (e.g. the cuffs that are aligned into the 'spine' structure) so that the cuffs provide a radiopaque reference that allows the stent(s) to be visible under fluoroscopic imaging. In some embodiments, a radiopaque marker may be in the form of an extruded metal tubing (e.g. made of a radiopaque material such as platinum-iridium, or other material such as those disclosed herein); the extruded tubing may be incorporated into the cuff in various ways, including by sliding the extruded tubing over a polymer cuff material. In other embodiments, radiopaque materials may be formed by covalently binding iodine to polymers that are incorporated into a device.

Radiopaque materials and elements may include: barium sulfate, bismuth subcarbonate, zirconium dioxide, cadmium, tungsten, gold, tantalum, bismuth, platinum, iridium, and rhodium. Radiopaque, physiologically-compatible materials may include metals and alloys selected from the Platinum Group metals, especially platinum, rhodium, palladium, rhenium, as well as gold, silver, and tantalum, and Group 6 metals (chromium, molybdenum, tungsten, and seaborgium) and alloys of these metals. These metals have significant radiopacity and in their alloy forms may be tailored to accomplish an appropriate blend of flexibility and stiffness, and are also largely biocompatible. One possible radiopaque material is a platinum/tungsten alloy, e.g., 8% tungsten and the remainder platinum. The particular form and choice of material used for the implantable frame will depend on the desired application. Therefore, if the cuffs are at least partially radiopaque, such that a significant portion of electromagnetic waves in various imaging modalities are unable to pass therethrough, the relative positioning and alignment of cuffs 200 and 200' may provide useful information when imaging the stent. By contrast, many bio-metals (including those used in the wires) are radiolucent and thus are not visible using standard X-ray or fluoroscopic imaging methods. Addition of radiopaque material in one or more cuffs (e.g. to a linear spine of cuffs 200 and 200') in ring-based stent 300 or net-based stent 400, or formation of two or more such spines of cuffs having radiopaque material (e.g. having two spines separated by 180 degrees when viewed in cross-section), creates both a method for simply visualizing the stents 300 and 400 under fluoroscopy as well as for accurately placing and confirming expansion of the stent in a blood vessel.

Although the radiopaque cuffs (or other mechanical securing mechanism) may be arranged such that their long axes are parallel with each other to aid in alignment, the cuffs need not necessarily be arranged in a straight line (i.e. such that an imaginary straight line could be drawn through all the cuffs). Instead, in various embodiments the cuffs may be arranged in any configuration deemed suitable for the placement, identification, (re)location, evaluation, or other perception or manipulation of the stent in situ. For example, instead of being arranged in a straight row, the cuffs (200, 200') may be provided on opposing sides in an alternating pattern, for example, of adjacent rings of the stent 300. In ring-based stents 300, for example as shown in FIG. 6 and discussed further below, the cuffs may be slightly staggered between adjacent rings and thus would not necessarily be coaligned with the long axis of the stent 300 and/or would not necessarily form a straight line.

In various embodiments the mechanical securing mechanism (i.e. the cuffs) need not be elongated, and in other embodiments the mechanism may not have a well-defined axis and/or the long axes of the mechanism may not be aligned with the long axis of the stent. Nevertheless, the securing mechanisms may be positioned relative to each other to provide a path or other indication of the long axis of the stent, regardless of shape.

FIG. 6 depicts a fully-assembled sinusoidal wave-form ring stent 300. Wire-formed rings 100 are interconnected by securing each of the rings' tails 120 into pre-positioned bridging cuffs 200' located on adjacent rings. In different configurations, wire tails 120 may be secured to the bridging cuffs 200', for example using a biocompatible adhesive such as cyanoacrylate injected into the joining cuffs 200 and bridging cuffs 200'. Each wire-formed ring may be independent from any adjacent ring(s) to which it is connected, helping improve the hoop strength of modular stent 300. By providing a stent formed of independent stent-modules, failure of one module (i.e. a wire-formed ring) need not necessarily compromise other modules in the stent.

Cuffs 200, 200' may be pre-mounted to struts 110 of each ring during the ring-forming process for stent 300. Bridging cuffs 200' may be slid onto the wire at various points in the formation of the ring, including for example before or after bending of the wire to form the sinusoidal or other shapes. The cuffs 200, 200' on stent 300 may span a portion (or substantially all) of the distance between the upper 102 and lower 106 crowns. Ring tails 120 may be tucked/inserted into joining cuff 200 to form a closed-ring with bridging cuffs 200' pre-mounted on struts 110 at specified intervals. The placement of bridging cuff 200' may vary based on, for example, the number of crowns per ring and stent length. In the six-crown ring shown in FIG. 3, for example, bridging cuffs 200' may be slid into place at a spacing of 180° from joining cuff 200. This spacing can facilitate and/or help ensure symmetrical expansion of the stent.

Figure 7:
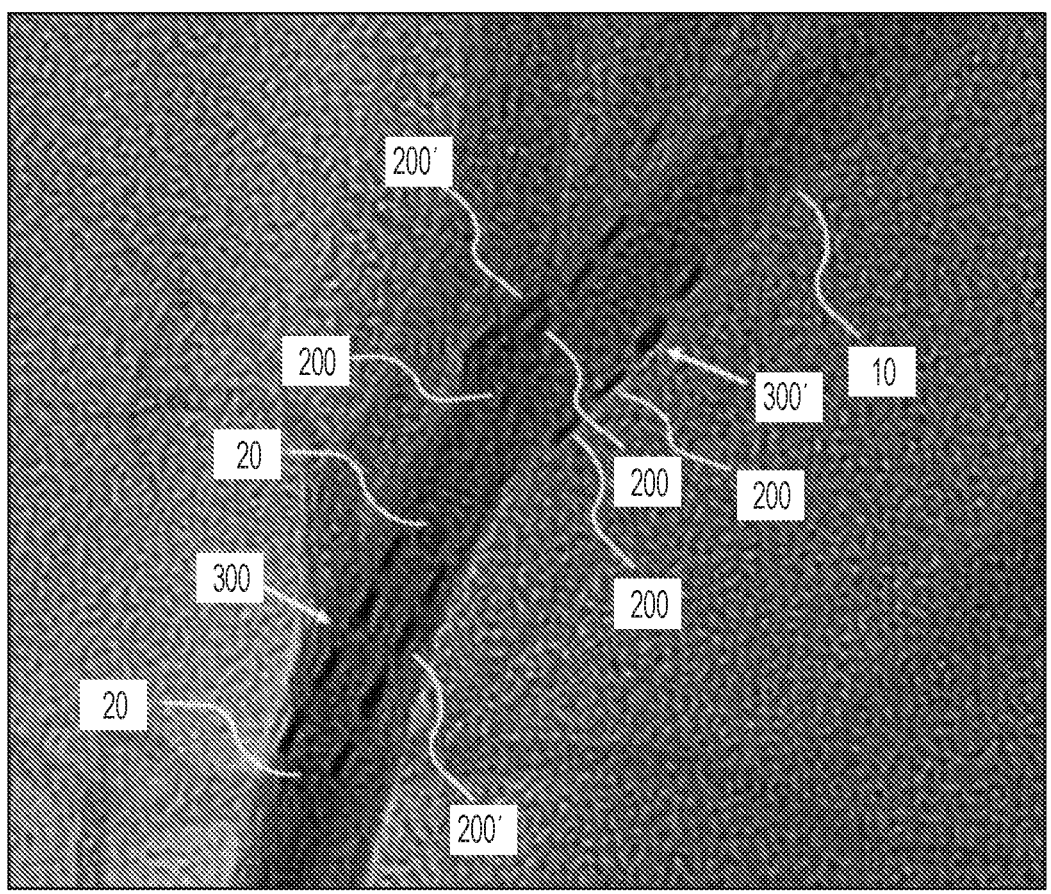
FIG. 7 is an image of an exemplary stent implanted in a blood vessel, with radiopaque cuffs visible via fluoroscopic imaging.

FIG. 7, for example, provides an image of two stents 300, 300' obtained under fluoroscopic imaging. Stent 300 (lower portion of FIG. 7) is in a pre-expansion state, mounted to a balloon delivery system that is also radiolucent (except for the two radiopaque markers 20 that are visible at either end of the stent as well as in the radiopaque cuffs 200 and 200' which make up the linear spines). In this configuration, the linear arrays of radiopaque cuffs (which form spines) allow stent 300, which is mounted on the radiolucent balloon delivery catheter, to be visualized while it is rotated until the linear spines are aligned with the walls of the blood vessels 10. This spine alignment method can facilitate and enhance precise placement and expansion of the stent when it is inflated. FIG. 7 also includes an image of an already-expanded stent 300' (upper portion of FIG. 7) aligned with another blood vessel, showing that the spines are spaced further apart than the spines of the pre-expansion stent 300.

In the expanded stent 300' shown in FIG. 7, the second ring from the bottom is pre-mounted with two radiopaque bridging cuffs 200'. In different configurations, each wire-formed ring stent may comprise at least two rings with parallel cuffs 200' (i.e. 'parallel' in the sense that the cuffs are separated on the ring and have axes that are approximately aligned with one another). In the version shown, the parallel cuffs 200' may serve both to secure adjacent rings as well as provide a fluoroscopic reference once the stent is expanded in the blood vessel. During the stent expansion procedure, the two parallel cuffs 200' separate indicating that expansion has occurred. This reference aids in delivery of the device.

Figure 8:
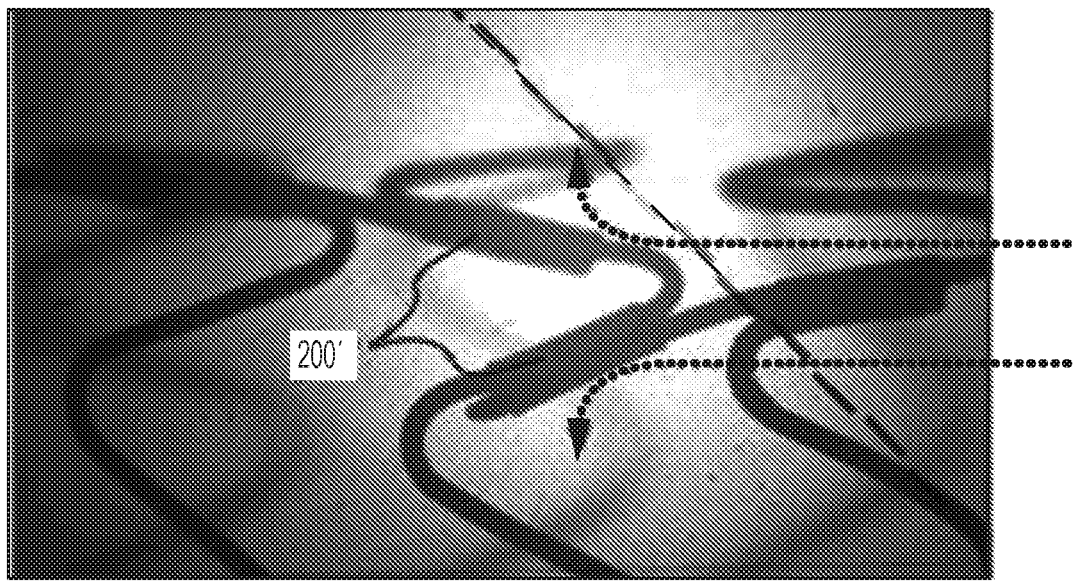
FIG. 8 is an image of an exemplary stent that has been expanded, with previously-parallel radiopaque cuffs spread apart. The adjacent cuffs ('dual cuffs') in this configuration secure the second and third rings (the 'inner rings') of a four-ring stent.
Figure 9:
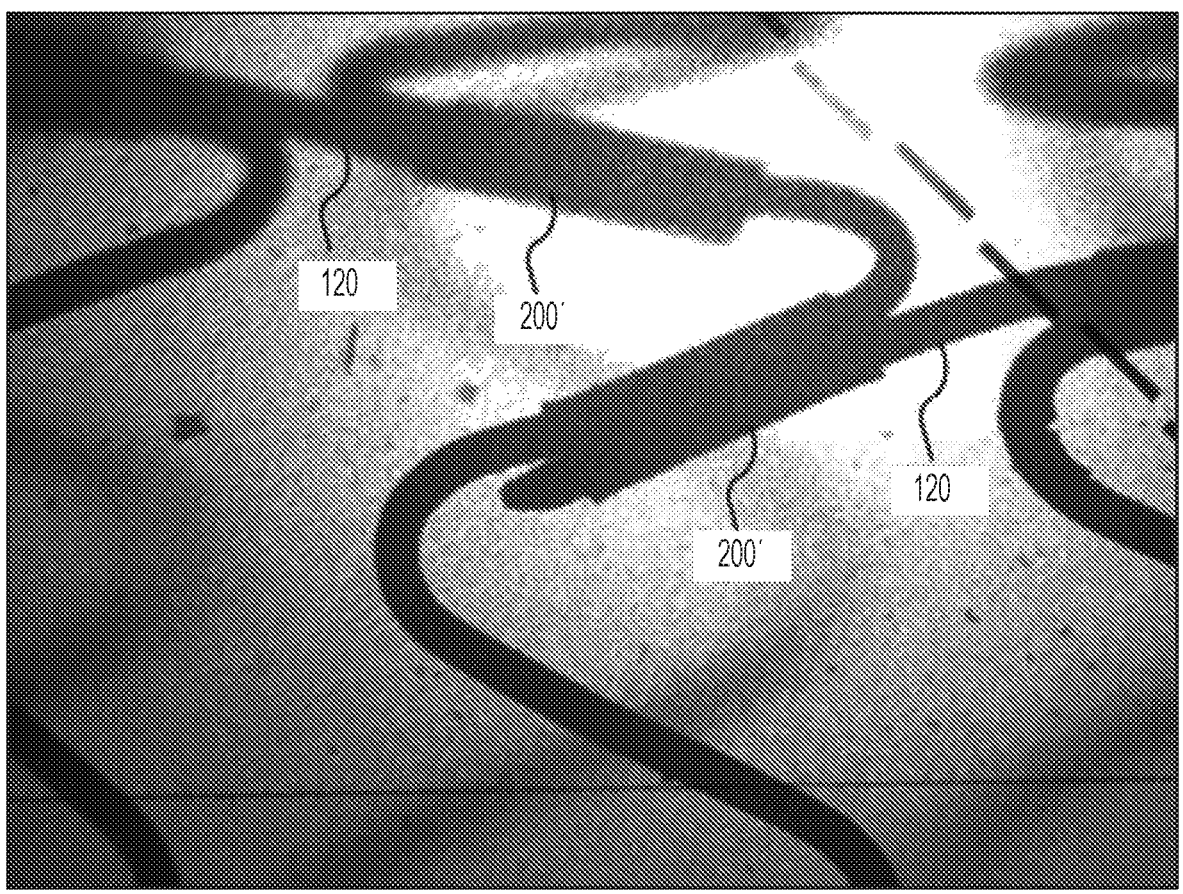
FIG. 9 is an image of an exemplary stent with wire tails functioning as joining cuffs that are received into cuffs to connect adjacent rings to one another.

In some embodiments, cuffs may start in a parallel configuration prior to expansion of the stent but then are changed to a different configuration as a result of expansion of the stent. For example, FIG. 8 provides an image of (previously) parallel cuffs 200' after expansion of stent 300 inside the blood vessel 10. The dotted lines and arrow heads depict proper cell expansion; that is, separation between the stent struts 110 such that struts 110 transition from being substantially parallel to one another to form a 'V' or 'L' shape. The term 'cell' here refers to the area or space created between two struts 110 during the expansion of the wire-formed ring 100. Radiopaque cuffs 200/200' on each side of the rings can provide a visual cue to help a clinician ensure that each ring is well-expanded and apposed against the wall of blood vessel 10. In such embodiments, the ring tails serve as bridging connectors that are received in bridging cuffs 200' to bridge adjacent rings as seen in FIGS. 8 and 9.

Figure 10:
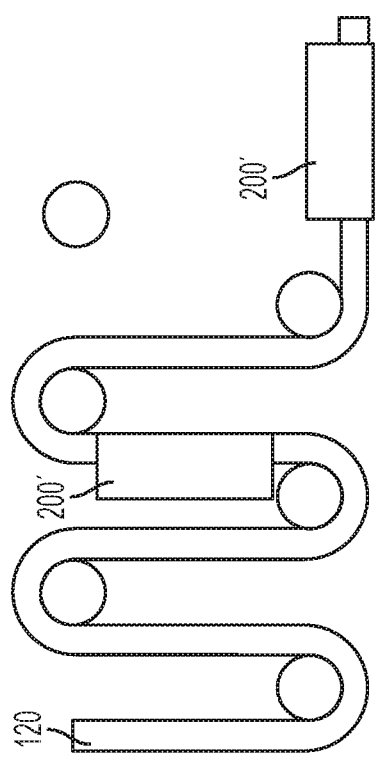
FIG. 10 represents an exemplary wire-forming process of using pins to bend and shape the wires as detailed in the text, during which bridging cuffs are slid into place at pre-determined locations on the wire.
Figure 11:
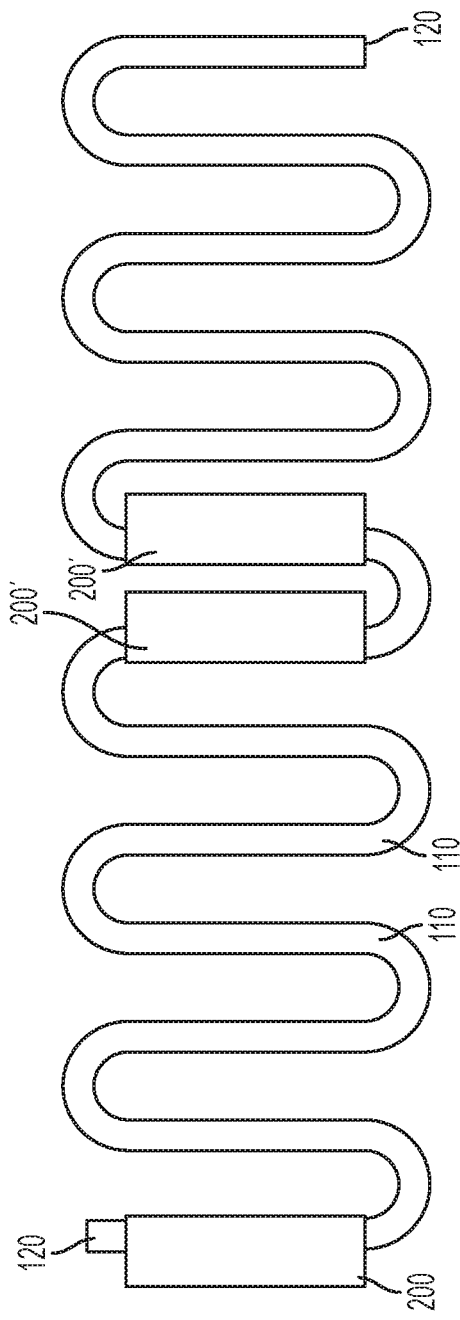
FIG. 11 depicts two parallel bridging cuffs on adjacent struts of an exemplary flattened wire-formed ring shown in a flat view.

As discussed above, bridging cuffs 200' may be placed on a wire during formation of a sinusoidal ring, as shown in FIG. 10. Referring to the exemplary wire-forming process of FIG. 10, which may involve bending or twisting the wire around one or more fixed pins or pegs (e.g. on a pin board), bridging cuffs 200' may be slid into place at pre-determined locations based on the number of apices (e.g., number of upper and lower crown portions) during the wire-forming process to achieve a desired connection pattern. The placement of a third, parallel joining cuff on an adjacent strut (110) as depicted in FIG. 11, may correspond with the number of rings to be incorporated in the stent (such as the one in FIG. 6, discussed above). The locations where cuffs are slipped into place depends in part on the number of crowns or peaks per ring, the number of rings in the final stent, etc.

Cuffs 200 and 200' can be made from a durable, a degradable, and/or a combination of durable, degradable, and, in certain embodiments, radiopaque material, including but not limited to platinum-iridium and polyimide. The joining cuffs with radiopaque elements such as platinum-iridium (or other materials as listed above) may be assembled in combination with non-absorbable polymers, such as polyimide, or with absorbable polymers, such as poly-lactide (PLA), poly(lactide-co-glycolide) (PLGA), or polylactone. The radiopaque material-filled cuffs may also be partially or fully insulated to prevent micro-galvanic corrosion and to eliminate or significantly reduce the galvanic potential of the differing elements.

Thus, in various embodiments, the cuffs of any of the disclosed embodiments may include one or more compounds from the following groups: polyphosphazenes, polyanhydrides, polyacetals, poly(ortho esters), polyphosphoesters, polycaprolactones, polyurethanes, polylactides, polycarbonates, and/or polyamides. The compounds may include one or more of: polyesters including poly-alpha hydroxy and poly-beta hydroxy polyesters, polycaprolactone, polyglycolic acid, polyether-esters, poly(p-dioxanone), polyoxaesters; polyphosphazenes; polyanhydrides; polycarbonates including polytrimethylene carbonate and poly(iminocarbonate); polyesteramides; polyurethanes; polyisocyantes; polyphosphazines; polyethers including polyglycols polyorthoesters; epoxy polymers including polyethylene oxide; polysaccharides including cellulose, chitin, dextran, starch, hydroxyethyl starch, polygluconate, hyaluronic acid; polyamides including polyamino acids, polyester-amides, polyglutamic acid, poly-lysine, gelatin, fibrin, fibrinogen, casein, collagen. The compounds may also include one or more FDA-approved materials including: polyglycolic acid (PGA), polylactic acid (PLA), Polyglactin 910 (comprising a 9:1 ratio of glycolide per lactide unit, and known also as VICRYLT.TM.), polyglyconate (comprising a 9:1 ratio of glycolide per trimethylene carbonate unit, and known also as MAXON.TM.), and polydioxanone (PDS). Other examples of suitable bioabsorbable materials which may be used include: poly(glycolic acid), poly(lactic acid), poly(epsilon-caprolactone), poly(dimethyl glycolic acid), poly(hydroxy butyrate), polydioxanone, copolymers of polylactic acid and polyethyleneoxide, poly(lactide-co-glycolide), poly(hydroxybutyrate-co-valerate), poly(glycolic acid-co-trimethylene carbonate), poly(epsilon-caprolactone-co-p-dioxanone), poly-L-glutamic acid or poly-L-lysine, polyhydroxyvalerate, poly(hydroxyalkanoates), poly(3-hydroxybutyrate), poly(4-hydroxybutyrate), poly(3-hydroxyvalerate), and poly (caprolactone), or poly(valerolactone), poly(1,3-dioxan-2-one), poly(6,6-dimethyl-1,4-dioxan-2-one), poly(1,4-dioxepan-2-one), and poly(1,5-dioxepan-2-one). Yet other examples of polymers that can be used include: polyorthocarbonates, poly(amino acids) such as polylysine, and biodegradable polyphosphazenes such as poly(phenoxy-co-carboxylatophenoxy phosphazene). In general, skilled artisans will understand that other materials may be used to make the cuffs; additional information regarding materials to be used for medical implants may be found in US Patent Appl. Publ. No. 2010/0262221, which is incorporated herein by reference in its entirety for all purposes.

Net-Based Bio-Metal Stents

Figure 12:
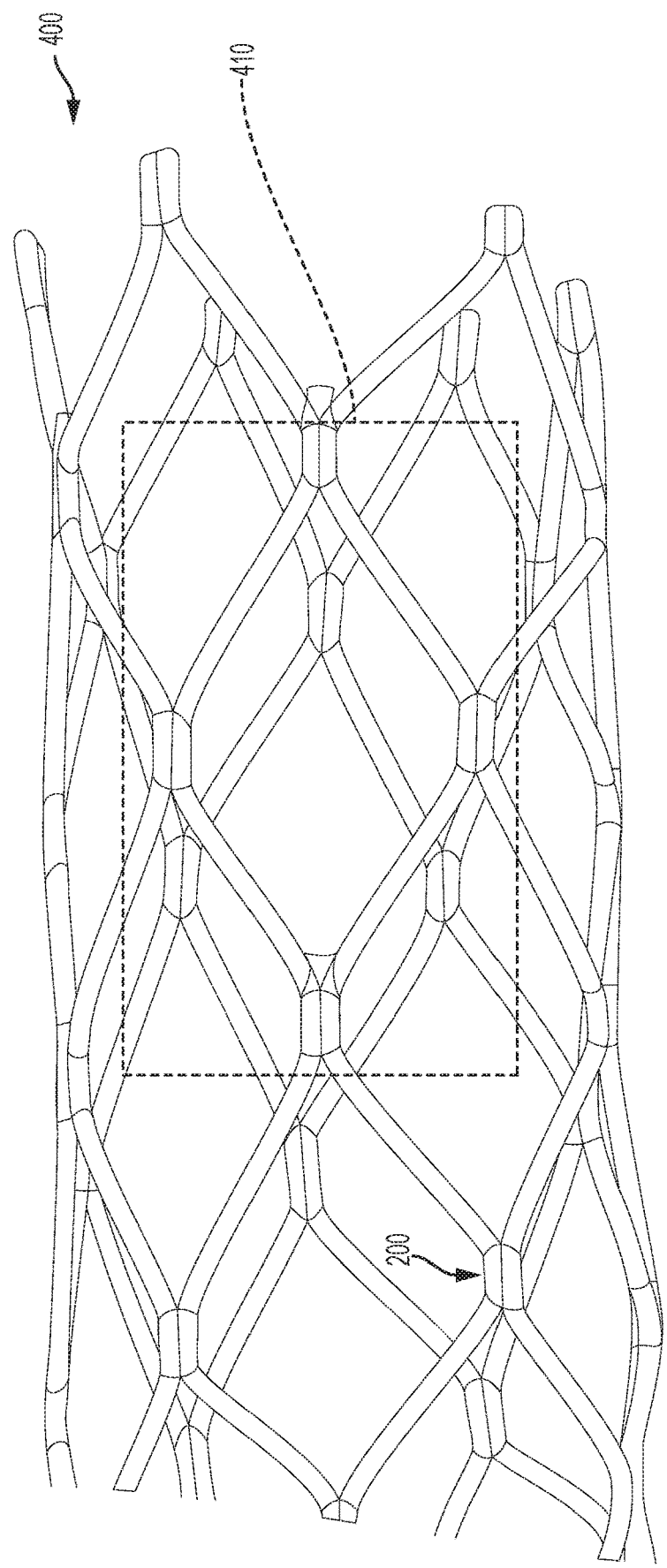
FIG. 12 is an image of an exemplary wire-formed, net-based stent structure produced according to the disclosed methods.
Figure 13:
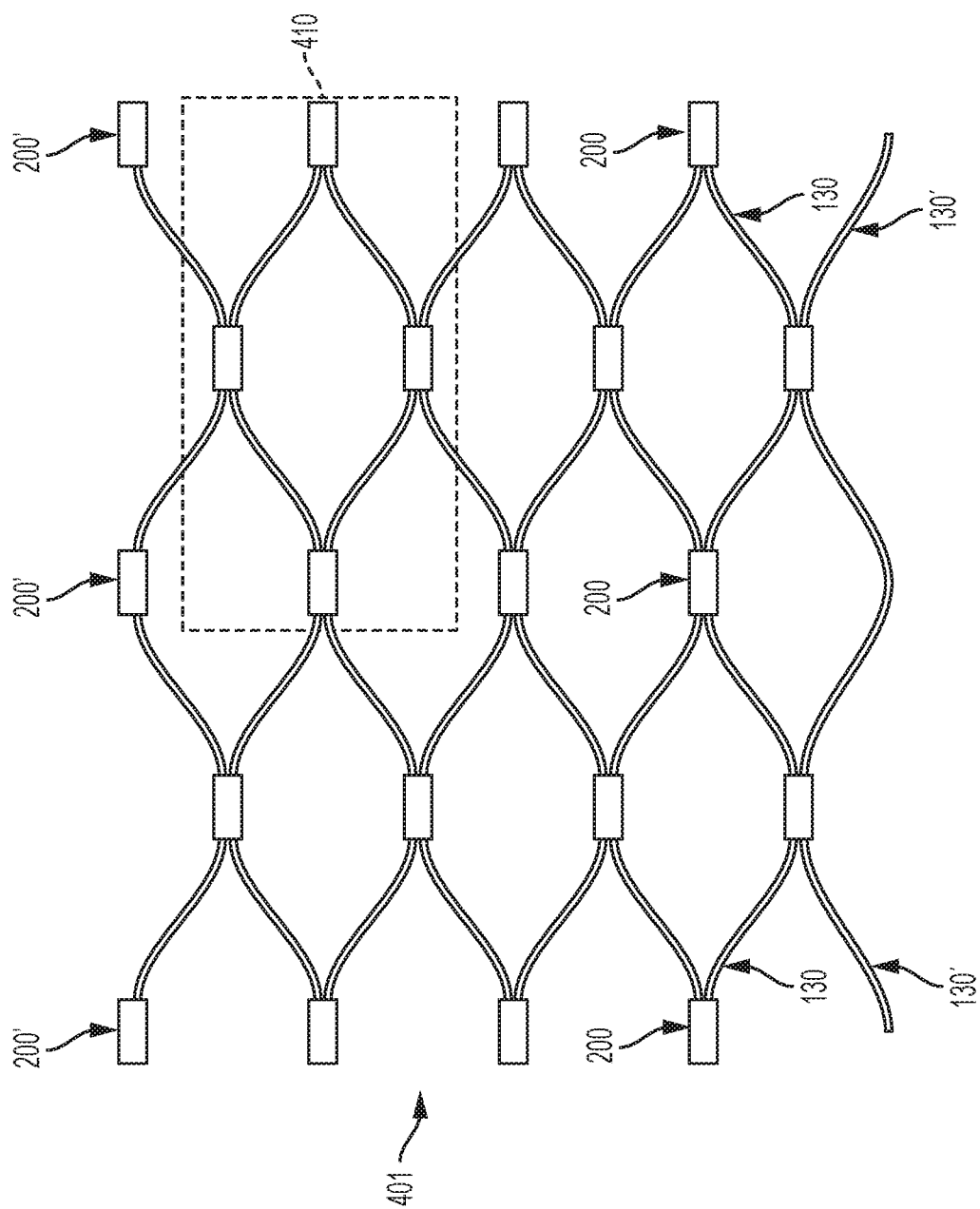
FIG. 13 is a flat-view representation of a net for use as an implant or for forming a net-based stent such as that shown in FIG. 12.

In another embodiment of a bio-metal stent 400 (e.g. as shown in FIGS. 12 and 13), an exemplary wire-formed net 401 may be produced by weaving wires through a plurality of joining cuffs 200 arranged in a pre-arranged pattern on a wire-forming fixture 500 (see FIG. 14A). The wires used to form the net 401, for example, may be threaded along the length of the wire-forming fixture 500 into a woven pattern, as depicted in FIG. 14.

FIG. 12 shows an image of a fully-assembled net stent 400 that has been expanded using a balloon. From FIG. 12 it can be seen that the expanded net stent 400 includes a number of diamond-shaped repeating units, or cells 410. The cells 410 are formed when wires 130 are inserted into pre-positioned joining cuffs 200 and the net structure 401 is wrapped around a mandrel; the cylindrical, net-based stent 400 is completed and stabilized by inserting end-wire 130' (sometimes referred to as a 'keystone' wire) into a particular subset of joining cuffs 200' along an edge of the net structure 401. Wire tails 120 at the end of the net 401 may be secured with a biocompatible adhesive (e.g. cyanoacrylate) injected into the bridging cuff 200'.

To form a net 401 (which can subsequently be used to produce a net-based stent 400), a number of joining cuffs 200 are placed in an array of cuff spacers 502 on the wire-forming fixture 500 (FIG. 14A). In some embodiments, the cuffs 200 may have an approximately oval or oblong cross-sectional shape which, when the cuffs 200 are placed into the cuff spacers 502, may be compressed into a rounded or approximately circular shape. Thus, following insertion of one or more wires into the cuffs 200 and subsequent removal of the cuffs 200 from the cuff spacers 502, the cuffs 200 may relax to their oblong shape and thereby provide a holding force to help keep the wires in the cuffs 200/keep the cuffs 200 from slipping out of position relative to the wire(s).

The fixture 500 depicted in FIG. 14A may be any suitable flat surface to which are attached a number of cuff spacers 502 in a desired array. The number and placement of cuff spacers 502 may be determined by the dimensions and property of the final net 401 that is produced. As shown in FIG. 14A the cuff spacers 502 may be placed in rows that are slightly offset from the adjacent row(s) so that a particular wire may be threaded through a series of cuffs in an approximate zigzag pattern (e.g. see FIG. 14B, which is a close-up view of a group of cuffs 200 that produce a single cell of the final net 401). A particular wire may be associated with two subsets of cuffs 200, a first subset through which it is coupled to a first adjacent wire and a second subset through which it is coupled to a second adjacent wire, where the members of each subset alternate along the particular wire. In certain embodiments, the stents 400 may have diameters between 1 mm and 15 mm and lengths may range between 1 mm to 200 mm. In various embodiments, the dimensions of the edges of the nets 401 may vary from 1 mm length/width to 500 mm length/width. In various embodiments, cuffs made of a durable material such as polyimide may have a wall thickness of approximately 0.002". In other embodiments, a cuff containing a radiopaque material such as platinum-iridium may have a wall thickness ranging from about 0.040" to about 0.032", depending on the particular application. The final thickness of the cuff that contains a radiopaque material may also be dependent on factors such as ultimate tensile and yield strength for the extruded metal tubing that is used (which also provides an indication of the malleability of the extruded tubing and its ability to be attached, e.g. by crimping, to the associated polymer cuff material). For polymer cuff materials, other factors that may influence the thickness of the cuff include: whether the cuff is made from a durable (non-absorbable) material vs. an absorbable material; availability of pre-made cuff material of a given thickness vs. ability to have cuff material made to a specified thickness; and/or the wire size.

The fixture 500 shown in FIG. 14A is not necessarily drawn to scale (e.g. the distance between adjacent rows of cuff connectors 502 may be proportionately much greater than shown in FIG. 14A) and may contain many more rows of cuff connectors 502, and each row may contain many more cuff connectors 502, than is shown. In addition, some of the cuffs 200 associated with wires at the edges of the net 401 (e.g. shown on the left and right sides of FIG. 14A) may have only a single wire threaded through them; these cuffs will then have an additional wire, specifically the end-wire or keystone wire, threaded through them once the net 401 has been rolled (e.g. around a mandrel) into a tube shape. The end-wire is threaded through cuffs on opposing edges of the rolled-up net 401 to hold the stent 400 together and maintain the tube shape. As noted previously, the cuffs 200 join together two portions of wire (from the same or different wires) at connection points between the wires, i.e. points where the wires are in proximity and possibly in contact and where the cuffs help to stabilize and maintain the wire(s) in certain positions.

Thus, in certain embodiments the net 401 may be configured by weaving wires through joining cuffs 200, with the result that adjacent parallel wires are connected to one another by a series of joining cuffs 200, forming a plurality of repeating cells 410, as depicted in FIG. 13. In general, two adjacent wires 130 pass through each joining cuff 200 following an arranged pattern on the wire-forming fixture 500 (until end-tails 120' are inserted into final common/shared cuffs and may or may not extend out from the joining cuff 200), allowing for adjacent parallel wires 130 and end-tails 120' to form a plurality of cells 410, for which the plurality of the cells make up net like structure to later be formed into a stent 400. Although the basic repeating cell 410 pattern shown in FIGS. 12-15 has a substantially 'diamond' shape, other repeating patterns (e.g. with one or more shapes including square, triangle, and/or rectangle) may be formed by the assembly of wires and cuffs 200, and in some embodiments not all of the basic unit or cell shapes may be the same but rather may vary in size, width, height, pitch, angle, etc.

FIGS. 15A-15D show various steps of converting a net 401 to a net-based stent 400. FIG. 15A shows a mandrel 600 around which a net 401 may be wrapped. Once the net 401 has been rolled up (indicated by the curved arrows in FIG. 15B) and wrapped around the mandrel 600, the edges of the net 401 are joined together by weaving an end-wire 130' (or keystone wire) through the cuffs 200' at the edges of the net 401. FIG. 15C shows the end-wire 201 (wavy dashed line) being woven through the cuffs 200' on the opposing edges of the net 401. Once the end-wire 130' has passed through the edge joining cuffs 200', this stabilizes the net 401 into a tube shape thereby creating the cylindrical net-shaped stent structure 400.

After wires have been inserted into the joining cuffs 200, 200', the cuffs may be joined with an adhesive (i.e. filled with a sealing material 201 (FIG. 15E) such as cyanoacrylate) and may also be sealed along their long axes to prevent fluid infiltration into the cuffs at the connection points. For example, once the wires are mechanically secured within the cuff, a sealing agent 201, including but not limited to fillers, adhesives, glues, polymers, such as epoxy, etc. may be added inside the cuffs 200, 200' (FIGS. 15D, 15E). In various embodiments the cuffs may be filled with one or more medical grade adhesive selected from: acrylics (e.g. cyanoacrylate), epoxies, and/or polyurethanes. Sealing the cuffed areas prevents premature degradation and thereby reduces the risk of mechanical failure of the wire. In some embodiments a first sealing agent 201 may be a relatively low viscosity material that cures and sets quickly in order to stabilize the wires within the cuffs, followed by a second sealing agent such as a higher viscosity material that completely seals the wires within the cuffs against fluid penetration. In various embodiments the cuffs may be sealed before the net 401 is removed from the fixture 500 in order to stabilize the wires and cuffs before removing the net 401.

In various embodiments a sealing material may be injected, e.g. through a fine needle or nozzle (e.g. attached to a pressure syringe), into the inside of the cuffs, where the material will cure and set. As discussed above, in certain embodiments a radiopaque material such as platinum-iridium may be added to the cuffs to allow the stents to be visualized using X-ray imaging technology and also to help confirm that the stent has been properly expanded within a patient's vessel or other luminal space. In some embodiments the platinum-iridium may be inserted into the cuff and then a sealing material may be added to the cuff to seal the cuff. In particular embodiments, non-degradable materials may be selected for the cuff and/or sealing compound when the cuff contains radiopaque material, in order to encapsulate the material and prevent its release.

As discussed above with regard to the ring-based stents 300, fewer than all of the cuffs 200 may include radiopaque material. The cuffs 200 containing radiopaque material may be selected so that they to form particular patterns (e.g. such as the 'spines' discussed above) which aid in placement and confirming proper deployment of the net-based stent 400. Given the relatively large number of cuffs 200 in the net-based stent 400 structure, determining which cuffs 200 to mark with radiopaque material is simplified since the stent 400 contains a regular array of cuffs 200 to work with. As with the ring-based stents, multiple linear arrangements or spines of cuffs 200 may be marked with radiopaque material, for example two such spines may be marked so that the spines are on opposite sides of the cylindrical structure of the stent 400, i.e. they may be separated by 180 degrees when the stent 400 is viewed in cross-section.

FIG. 15D shows a single joining cuff 200 having two wires running through it and sealing material 201 disposed inside. FIG. 15E, which corresponds to dashed line E-E' in FIG. 15D, shows a cross-sectional view through a sealed cuff 200. The wires 130 running through the cuff 200 are shown to be surrounded by the sealing material 201, which may include a radiopaque material and/or a sealant. In certain embodiments, the joining cuffs 200 may be made of a non-absorbable polymer such as polyimide or an absorbable polymer such as poly-lactide (PLA), poly(lactide-co-glycolide) (PLGA), or polylactone. In various embodiments the cuffs 200 may have an inside diameter of 0.20-0.50 mm, and in particular embodiments the inside diameter may be 0.35 mm. In other embodiments the cuffs may have a length ranging from 0.25-1.0 mm and in particular embodiments the length may be 0.75 mm. In certain embodiments, a 'cuff' may in fact be two or more segments of cuff material that are placed near each other to stabilize a particular connection point between two wires or segments of wire. In general the cuffs need to be strong enough to hold the net (or rings) together but sufficiently flexible and resilient to permit the stent to expand and to withstand movements associated with normal use during and after being implanted. Finally, it should be noted that the apparatus and methods for producing the net-based bio-metal stents can be used to produce the ring-based bio-metal stents, and vice versa.

Uses of Implants and Stents

In various embodiments, the net 401 may be used in its flat form as a bioabsorbable implant or, as discussed further below, may be rolled and secured into a tubular shape to be used as a net-based stent 400. The flat net 401, the tubular net-based stent 400, or the ring-based stent 300 may be used within or outside the vascular system. In certain embodiments, the tubular ring-based stent 300 and/or net-based stent 400 may be placed inside a luminal structure of a subject including structures of the vascular, lymphatic, or gastrointestinal systems as well as various organ ducts. In particular embodiments, the flat net 401 and/or tubular configuration (i.e. stent 300 or stent 400) may be used a scaffold for soft tissue injury; as a closure or fixation device for soft tissue or bone; and/or as a filler. In those embodiments in which the net 401 or stent 300/stent 400 is implanted into a non-vascular environment, the particular therapeutic agents and/or other coating materials may be changed to suit the particular tissue environment.

The present invention has been described in terms of one or more preferred versions, and it should be appreciated that many equivalents, alternatives, variations, additions, and modifications, aside from those expressly stated, and apart from combining the different features of the foregoing versions in varying ways, can be made and are within the scope of the invention. The true scope of the invention will be defined by the claims included in any later-filed utility patent application claiming priority from this provisional patent application.

What is claimed is:

1. A bio-metal implant comprising:
a first magnesium alloy wire adjacent a second magnesium alloy wire at a first connection point,
each of the first magnesium alloy wire and the second magnesium alloy wire extending from a first end of the implant to a second end of the implant,
an end of the first magnesium alloy wire coupled to an end of the second magnesium alloy wire at the first connection point using a first joining cuff of a plurality of joining cuffs,
the first joining cuff being located at the first end of the implant,
the end of the first magnesium alloy wire and the end of the second magnesium alloy wire both being inserted into the first joining cuff,
the first magnesium alloy wire and the second magnesium alloy wire being shaped to form at least a portion of the bio-metal implant,
and
at least two joining cuffs of the plurality of joining cuffs each comprising a radiopaque material, such that the at least two joining cuffs are configured to move apart from one another upon expansion of the bio-metal implant.

2. The bio-metal implant of claim 1, wherein the first magnesium alloy wire and the second magnesium alloy wire each has a sinusoidal shape.

3. The bio-metal implant of claim 1, wherein the first magnesium alloy wire is further coupled to the second magnesium alloy wire at a first plurality of connection points by a first subset of the plurality of joining cuffs.

4. The bio-metal implant of claim 3, further comprising a third magnesium alloy wire coupled to the second magnesium alloy wire at a second plurality of connection points by a second subset of the plurality of joining cuffs, different from the first sub set,
each of the second plurality of connection points being alternated with each of the first plurality of connection points along the second magnesium alloy wire,
wherein the first magnesium alloy wire, the second magnesium alloy wire, and the third magnesium alloy wire define a net structure.

5. The bio-metal implant of claim 4, wherein the net structure is formed into a tube shape.

6. The bio-metal implant of claim 5, wherein the net structure is secured into the tube shape using a magnesium alloy end wire attached to opposing edges of the net structure.

7. The bio-metal implant of claim 1, wherein each of the plurality of joining cuffs comprises a sealing material.

8. A bio-metal implant comprising:
   a plurality of magnesium alloy wires formed into a tube,
      each of the plurality of magnesium alloy wires extending from a first end of the implant to a second end of the implant,
      each end of each of the plurality of magnesium alloy wires being secured to an end of an adjacent magnesium alloy wire of the plurality of magnesium alloy wires by insertion of the ends into respective joining cuffs of a plurality of joining cuffs at the first end of the implant or the second end of the implant, and
      at least two joining cuffs of the plurality of joining cuffs each comprising a radiopaque material, such that the at least two joining cuffs are configured to move apart from one another upon expansion of the bio-metal implant.

9. The bio-metal implant of claim 8, wherein each joining cuff of the plurality of joining cuffs has two magnesium alloy wires of the plurality of magnesium alloy wires inserted therein.

10. The bio-metal implant of claim 8, wherein each of the plurality of cuffs comprises a sealing material.

* * * * *